United States Patent [19]

Schmidhammer et al.

[11] 4,188,347
[45] Feb. 12, 1980

[54] PROCESS FOR TREATING UNREACTED 1,2-DICHLOROETHANE FROM 1,2-DICHLOROETHANE CRACKING

[75] Inventors: Ludwig Schmidhammer, Haiming; Hellmuth Frey, Burghausen, both of Fed. Rep. of Germany

[73] Assignee: Wacker-Chemie GmbH, Munich, Fed. Rep. of Germany

[21] Appl. No.: 966,832

[22] Filed: Dec. 6, 1978

[30] Foreign Application Priority Data

Dec. 9, 1977 [DE] Fed. Rep. of Germany ....... 2754891

[51] Int. Cl.$^2$ ............................................. C07C 17/00
[52] U.S. Cl. ................................................. 260/652 P
[58] Field of Search ..................................... 260/652 P

[56] References Cited

U.S. PATENT DOCUMENTS

| 3,624,169 | 11/1971 | Fruhwirth | 260/654 H |
| 3,850,999 | 11/1974 | Gehrmann et al. | 260/654 H |
| 3,898,294 | 8/1975 | Cooley | 260/655 |
| 3,920,761 | 11/1975 | Kromg | 260/656 R |
| 4,125,564 | 11/1978 | Iwasaki et al. | 260/654 H |

Primary Examiner—Arthur P. Demers
Attorney, Agent, or Firm—Joel G. Ackerman

[57] ABSTRACT

An improved process for removal of chloroprene from 1,2-dichloroethane recovered unconverted from the effluent of 1,2-dichloroethane pyrolysis. The chloroprene is chlorinated with chlorine in the presence of o- or m-cresol or a chlorinated derivative thereof, and the excess chlorine from this step is removed by reaction with ethylene.

5 Claims, No Drawings

PROCESS FOR TREATING UNREACTED 1,2-DICHLOROETHANE FROM 1,2-DICHLOROETHANE CRACKING

BACKGROUND AND PRIOR ART

Vinyl chloride is produced commercially by the pyrolysis of 1,2-dichloroethane. The rate of conversion increases with the temperature and, the higher the temperature, the more undesired byproducts are generated during the cracking process. Following the separation of hydrogen chloride and vinyl chloride and the simultaneous extraction of traces of low-boiling byproducts such as 1,3-butadiene, acetylene, monovinyl-acetylene and methyl chloride, the 1,2-dichloroethane which has not been reacted during the cracking process still contains 1,1-dichloroethylene, chloroform, carbon tetrachloride, trichloroethylene, benzene and, above all, substantial quantities of 2-chlorobutadiene-1,3 and some 1-chlorobutadiene-1,3. In recycling the unreacted 1,2-dichloroethane, the elimination of these byproducts has been found to be necessary to prevent the plugging of the cracking furnace with soot and coke.

The removal of the above-mentioned byproducts by distillation has the drawback of resulting in the accumulation and subsequent polymerization of the chloroprene in the distillation column, causing operational difficulties.

From U.S. Pat. No. 3,876,714, it is generally known that, prior to the separation of the vinyl chloride and hydrogen chloride from the unconverted dichloroethane small amounts of chlorine can be added to the cracked gas containing the 1,2-dichloroethane. Following the addition of the chlorine, the liquid reaction mixture must be kept for a certain period of time in a storage tank before it can be further processed. Aside from the fact that this method does not eliminate all of the previously mentioned problems, it requires that in order to eliminate the danger of corrosion, special preventive measures be taken or that apparatus made of extremely fine and very expensive materials be employed.

A process is disclosed in U.S. Pat. No. 3,920,761 in which 0.01 to 1.0 weight % chlorine (based on the weight of the dichloroethane originally used) is added, dissolved in 1,2-dichloroethane, prior to the separation of vinyl chloride. Under the prevailing conditions, a portion of the chlorine reacts with the vinyl chloride to produce valueless 1,1,2-trichloroethane and a portion of the unreacted dichloroethane is partially substituted. Thus, a quantitative chlorination of chloroprene cannot be observed.

According to German Pat. No. 2,416,786, during the processing of the reaction products of a thermal cracking of 1,2-dichloroethane, the part of the column in which the high boiling products are to be separated is flushed with chlorine gas without a catalyst being present, after the hydrogen chloride and the vinyl chloride have been separated. The resulting decrease in chloroprene extends the time span over which the cracking furnace and the column may be used; however, a quantitative extraction of chloroprene, which is necessary in order to extend the time span over which the cracking furnace may be utilized, can still not be achieved. The simultaneous presence of chlorine in the distillation bottoms at temperatures of about 100° to 110° C. results in a noticeable chlorine substitution of the 1,2-dichloroethane, generating high-boiling 1,1,2-trichloroethane and is thus detrimental for economic reasons.

Consequently, the purpose of this invention is to provide a process for treating unreacted 1,2-dichloroethane from 1,2-dichloroethane cracking, prior to recycling, in which troublesome byproducts, especially 1,2-chlorobutadiene-1,3 and 2-chlorobutadiene-1,3 are eliminated in a simple and suitable manner while avoiding the drawbacks of the previously known methods and while increasing the period of time over which the pyrolysis reactor and the column can be operated.

SUMMARY OF THE INVENTION

The subject of this invention is thus a process for the removal of chloroprene from a stream comprising 1,2-dichloroethane recovered unconverted from 1,2-dichloroethane cracking, from which hydrogen chloride and vinyl chloride are separated, with said process being characterized by the fact that, prior to recycling, the remaining residue is mixed with one or a mixture of hydroxyl-containing aromatic compounds of the o-cresol or m-cresol type, or their mono- or dichloro derivatives, in quantities of from about 0.0001 to about 0.01 weight % relative to the unreacted 1,2-dichloroethane, in a chlorination step and a subsequent dechlorination step at temperatures from about 0° to about 80° C. and preferably from about 20° and to about 30° C., at pressures from about 0.5 to about 6 bars; and that dechlorination of the excess chlorine, which may be permitted to be as high as 800 ppm, is performed by adding an equivalent amount of ethylene after the chlorination step. The 1,2-dichloroethane is subsequently removed by distillation.

In a preferred embodiment of the invented process, up to 1% by volume of oxygen is added to the chlorine.

DETAILED DESCRIPTION OF THE INVENTION

Following the pyrolysis reaction, the uncracked 1,2-dichloroethane is drawn from the collection tank together with impurities and brought with the aid of suitable counterflow heat exchangers to a temperature of from about 0° to about 80° C., preferably about 20° to 30° C. and pressure from about 0.5 to about 6 bars. The hydroxyl-containing aromatics (o- or m-cresol and/or their mono- or dichloro derivatives) are kept in the liquid state in a heated storage container and are added by dissolving in warm 1,2-dichloroethane and supplying the solution by means of a dosing pump to the uncracked dichloroethane. The cresol or cresols are added in an amount of from about 0.0001 to about 0.01 weight %, relative to the unconverted 1,2-dichloroethane. The dichloroethane-cresol solution may alternatively be added to the unconverted dichloroethane before it is passed through the heat exchangers. The stream of dichloroethane, now containing the added cresol, is then passed to a chlorination zone or reactor.

The subsequent selective chlorination of the chlorobutadiene isomers present in the unreacted 1,2-dichloroethane may be carried out in an empty or a packed reaction tube. In order to provide for a better distribution of the ethylene, it is preferable that the dechlorination reactor consist of a packed tube. The chlorine source may consist of vaporized liquid chlorine or electrolysis chlorine to which, if necessary, enough oxygen has been added to achieve a maximum oxygen content of 1% by volume. If the oxygen content is higher than 1% by volume, there arises a danger that explosive gas mixtures may form in downstream equipment. The reaction tubes used in the process may be made of conventional carbon steels; more costly specialty steels are not required for this process. The contact time in the reactors should be from about 20 to about 50 seconds for the chlorination reaction and about 10 to about 40 seconds for the dechlorination reaction. The diameter-to-length ratio of the reaction tubes is not critical, however, it is desirable that the diameter:length ratio be selected so that in addition to the required contact time, the reactants are also thoroughly mixed in the tube. The preferred packing for the chlorination and dechlorination reactors is iron Raschig rings. Other packings such as ceramics or polytetrafluoroethylene may alternatively be used. The dechlorination reaction is preferably conducted under as high a pressure as possible, up to 6 bar, for better ethylene distribution.

The hydroxyl-containing aromatics which are added pursuant to this invention are partially chlorinated and extracted together with the other high-boiling components at the bottom of the heavy ends column. This prevents interference with the circulation of the dichloroethane when the latter is recycled to the pyrolysis furnace.

The amount of chlorine introduced into the chlorination zone for the chlorination of the 1-chlorobutadiene-1,3 and 2-chlorobutadiene-1,3, is measured so that following the chlorination step there is a maximum chlorine excess of 800 ppm. Experience has proven that for each mole of 2-chlorobutadiene-1,3 contained in the unreacted 1,2-dichloroethane, 1.2 to 1.7 moles of chlorine must be used and that for each mole of 1-chlorobutadiene-1,3, 2.1 to 2.3 moles of chlorine must be used. The byproducts 1-chlorobutadiene-1,3 and 2-chlorobutadiene-1,3, which are extremely bothersome in the unreacted 1,2-dichloroethane, are quantitatively chlorinated into harmless high-boiling products, without the occurrence of a noticeable substitution of 1,2-dichloroethane to 1,1,2-trichloroethane and without the formation of ethyl chloride (by reaction between ethylene and traces of hydrogen chloride in the presence of traces of iron salts, which may form on the steel equipment).

The invented process has the advantage that no 1,2-dichloroethane, practically no ethylene, and no chlorine are lost. It is surprising that such small quantities of the aforementioned hydroxyl-containing aromatics are sufficient to achieve quantitative chlorination of the chlorobutadiene isomers and that after a very short period in the chlorination zone, the excess chlorine can immediately be removed with ethylene. Without the addition of the aforementioned type of aromatics containing hydroxyl groups, even when traces of iron chloride are present as a chlorination catalyst, equimolar ethylene only reacts with dissolved free chlorine to the extent of 40%, while a major portion of the chlorine substitutes 1,2-dichloroethane, forming 1,1,2-trichloroethane.

The following represent illustrative examples of the conduct of the invention and comparisons in which the invention is not utilized. All figures given in ppm are by weight.

EXAMPLE 1

A stream of 30 tons per hour of unreacted 1,2-dichloroethane, containing 6 ppm 1,1,2-trichloroethane, 10 ppm ethyl chloride, 1500 ppm 2-chlorobutadiene-1,3 and 150 ppm 1-chlorobutadiene, which collects at the bottom of the vinyl chloride column, with a pressure of 5 bars and a temperature of 152° C., is cooled to 30° C. by means of a cooling apparatus. There is continuously added a stream of 10 ppm of o-cresol, diluted in 1,2-dichloroethane. Subsequently the dichloroethane is treated with 0.843 kmol per hour of vaporized liquid chlorine in an empty reaction tube (diameter 250 mm. length 5000 mm.) with the result that at the exit of the chlorination zone the chlorobutadiene isomers in the unreacted 1,2-dichloroethane are reduced to less than 1 ppm, while the 1,1,2-trichloroethane concentration, with an excess of 460 ppm of free chlorine, increases to only 176 ppm. Immediately after it leaves the chlorination zone, the unreacted 1,2-dichloroethane reaches a tube (diameter 220 mm. length 3800 mm.) filled with iron Raschig rings in which it is treated with 0.1944 kmol per hour of ethylene, with the result that the free chlorine present is nearly quantitatively converted into 1,2-dichloroethane, without any increase in the ethyl chloride content of the unreacted 1,2-dichloroethane. Following the dechlorination stage, the unreacted 1,2-dichloroethane contains only 2 ppm free chlorine, corresponding to an ethylene conversion of 99.6%.

EXAMPLE 2

(Comparison Example)

As in Example 1, 30 tons per hour of unreacted 1,2-dichloroethane with the same impurities is treated sequentially and without the presence of o-cresol, with 1.247 kmol per hour of vaporized liquid chlorine and 0.1944 kmol per hour of ethylene under identical reaction conditions. Even though this results in an excess of 460 ppm free chlorine in the chlorination zone, the unreacted 1,2-dichloroethane, after it has left the chlorination zone, still contains 20 ppm of 2-chlorobutadiene-1,3 in addition to 2000 ppm of 1,1,2-trichloroethane which has been generated by the chloro-substituted of 1,2-dichloroethane. Downstream from the dechlorination zone the 1,1,2-trichloroethane content increases to 2,140 ppm and the unreacted 1,2-dichloroethane leaving the dechlorination zone contains not only 30 ppm of ethyl chloride, which was generated by reaction between ethylene and hydrogen chloride, but also 200 ppm of free chlorine and about 110 ppm of ethylene (corresponding to an ethylene conversion of 40%). The latter mainly escapes as a gas in the nonpressurized downstream vessels and is thus lost. By substitution reaction with 1,2-dichloroethane, and chlorination of the residual 2-chlorobutadiene-1,3, the free chlorine which is still present partially decreases to approximately 100 ppm, causing the level of 1,1,2-trichloroethane in the unreacted 1,2-dichloroethane in the downstream equipment to increase to about 2,300 ppm. Additionally, the presence of free chlorine and sizeable quantities of hydrogen chloride (generated during the substitution chlorination of 1,2-dichloroethane), causes considerable environmental and corrosion problems relative to the downstream exhaust gases, which requires their scrubbing.

EXAMPLE 3

20 tons per hour of unreacted 1,2-dichloroethane derived from thermal cracking of 1,2-dichloroethane to vinyl chloride and hydrogen chloride, containing 5 ppm 1,1,2-trichloroethane, 7 ppm ethyl chloride, 1000 ppm 2-chlorobutadiene-1,3 and 120 ppm 1-chlorobutadiene-1,3, is continuously mixed with 15 ppm m-cresol as in Example 1, and then heated to 32° C. Subsequently the unreacted 1,2-dichloroethane is treated in the same empty reaction tube as described in Example 1, with 0.404 kmol per hour of electrolysis chlorine containing about 0.6% by volume of oxygen, with the result that, at the outlet of the chlorination zone the unreacted 1,2-dichloroethane contains less than 1 ppm of chlorobutadiene isomers, while with an excess of 350 ppm free chlorine, the 1,1,2-trichloroethane concentration increases to only 165 ppm. Immediately after it has left the chlorination zone, the unreacted 1,2-dichloroethane is treated with 0.099 kmol per hour of ethylene in the same reaction tube which was used in Example 1, with the result that the free chlorine present is converted almost quantitatively into 1,2-dichloroethane, without any increase in the original level of ethyl chloride and without any further increase of substitution products of the 1,2-dichloroethane. The unreacted 1,2-dichloroethane leaving the dechlorination zone contains only 1 ppm free chlorine, indicating an ethylene conversion of 99.99%.

EXAMPLE 4

The process of Example 3 is repeated, but without the addition of m-cresol. 20 tons per hour of unreacted 1,2-dichloroethane with the same impurities is treated sequentially with 0.565 kmol per hour of electrolysis chlorine and 0.348 kmol per hour of ethylene. Downstream from the chlorination zone the unreacted 1,2-dichloroethane contains, in addition to 550 ppm free chlorine, 900 ppm 1,1,2-trichloroethane and 40 ppm 2-chlorobutadiene-1,3. The latter cannot be removed in the following dechlorination zone since the free chlorine has been reacted off due to the increased addition of ethylene, in stoichiometric excess. The effluent from the dechlorination zone contains 5 ppm free chlorine, 25 ppm ethyl chloride, 960 ppm 1,1,2-trichloroethane and 0.238 kmol/hour of ethylene, corresponding to a conversion of 37.6%; most of the latter is lost in the unpressurized downstream equipment for unreacted 1,2-dichloroethane. In order to permit quantitative removal of the chloroprene, the ethylene must be introduced downstream from the dechlorination zone in order to provide for an additional contact time for the reaction between the chlorine and 2-chlorobutadiene-1,3.

EXAMPLE 5

In a manner analogous to Example 1, at 20° C. and a pressure of 3 bars and in the presence of 5 ppm o-cresol and 5 ppm m-cresol, 30 tons per hour of unreacted 1,2-dichloroethane having the same composition as in Example 1, is contacted first with 0.927 kmol/hour of evaporated liquid chlorine and then with 0.302 kmol/hour of ethylene. The unreacted 1,2-dichloroethane leaving the dechlorination zone contains the following compounds:

10 ppm ethyl chloride;
less than 1 ppm 2-chlorobutadiene-1,3;
less than 1 ppm 1-chlorobutadiene-1,3;
74 ppm 1,1,2-trichloroethane;
1 ppm free chlorine; and
no ethylene

What is claimed is:
1. A process for the removal of chloroprene from a stream comprising 1,2-dichloroethane recovered unconverted from the products of a 1,2-dichloroethane pyrolysis comprising:
 (a) contacting the stream at a temperature of from about 0° C. to about 80° C. with chlorine in the presence of from about 0.0001 to about 0.01 weight percent relative to the unconverted 1,2-dichloroethane of a substance selected from the group consisting of ortho-cresol, meta-cresol, chlorinated derivatives of ortho- and meta-cresols, and mixtures thereof, the amount of chlorine utilized being such as to produce a maximum chlorine content in the stream, after contact, of 800 ppm by weight; and
 (b) subjecting the chlorine-containing stream from step (a) to dechlorination by contact with an amount of ethylene equivalent to the chlorine content at a temperature of from about 0° C. to about 80° C.
2. A process according to claim 1 further comprising distilling the product of step (b) to remove components boiling higher than 1,2-dichloroethane.
3. A process according to claim 1 in which the chlorine contains oxygen, in a maximum content of 1% by volume.
4. A process according to claim 1 in which the temperature of step (a) is from about 20° C. to about 30° C.
5. A process according to claim 1 in which the temperature of step (b) is from about 20° C. to about 30° C.

* * * * *